United States Patent [19]

Yousif

[11] Patent Number: 5,103,838
[45] Date of Patent: Apr. 14, 1992

[54] DENTAL NIGHT GUARD

[76] Inventor: Edward N. Yousif, 5411 N. Artesian, Apt. B, Chicago, Ill. 60625

[21] Appl. No.: 477,750

[22] Filed: Feb. 9, 1990

[51] Int. Cl.⁵ ............................................. A61C 5/14
[52] U.S. Cl. .................................. 128/859; 128/861
[58] Field of Search ........................... 128/859–862, 128/62 A

[56] References Cited

U.S. PATENT DOCUMENTS

| | | | |
|---|---|---|---|
| 2,705,492 | 4/1955 | Chandler | 128/862 |
| 2,706,478 | 4/1955 | Porter | 128/862 |
| 2,750,941 | 6/1956 | Cathcart | 128/862 |
| 2,833,278 | 5/1958 | Ross | 128/862 |
| 3,124,129 | 3/1964 | Grossberg | 128/862 |
| 3,211,143 | 10/1965 | Grossberg | 128/862 |
| 3,236,235 | 2/1966 | Jacobs | 128/862 |
| 3,303,844 | 2/1967 | Johnson | 128/862 |

Primary Examiner—Robert A. Hafer
Assistant Examiner—Michael Brown
Attorney, Agent, or Firm—Willian Brinks Olds Hofer Gilson & Lione

[57] ABSTRACT

A dental guard is provided with a two layer construction wherein a soft layer is bonded to a hard layer. The soft layer makes contact with the user's upper set of teeth while the hard layer forms the exterior of the dental guard. The soft layer provides a dental guard which is comfortable to wear and less stressful on the user's teeth while the hard layer provides the desired durability.

15 Claims, 1 Drawing Sheet

DENTAL NIGHT GUARD

BACKGROUND OF THE INVENTION

1. Field of the Invention

The present invention is generally directed to dental guards worn by people to protect their teeth from the effects of grinding, and particularly, to an improved dental guard which is constructed of two layers: a soft layer, which contacts the user's teeth, bonded to a hard layer.

2. Description of the Prior Art

For many different reasons, some people grind their teeth, particularly during sleep. Depending upon the strength and frequency of the grinding, a person's teeth can be seriously damaged. To prevent the damage resulting from grinding, dental professionals often prescribe for their patients a dental protector, commonly referred to as a night guard, and also known as a stint. The dental guard acts as a protective barrier between the upper and lower sets of teeth, and is typically worn at night while the patient sleeps. Specifically, the dental guard covers the upper set of teeth, thus separating both sets of teeth.

There are two basic types of dental guards, referred to herein as a "hard guard" and a "soft guard." The hard guard is usually made from an acrylic. It is very inflexible and once formed cannot readily be altered. The soft guard is usually made out of a resin and is very flexible. A common resin used is a sheet resin mouth guard material sold by Healthco.

There are many types of problems associated with both of these guards. First, with respect to the hard guard, it usually is uncomfortable for most wearers because of its inflexible structure. In addition, it is very stressful to the teeth. Not only does the hard guard's structure create difficulty in wearing the device, but it also creates difficulties in removing it. It is not uncommon for persons with crowns to have them chipped by the hard guard. Also loose teeth may be pulled out by the guard. In addition, because of its inflexible structure, it often does not fit the mouth well, and therefore may bounce off the teeth and fall out of the user's mouth.

There are also problems associated with the soft guard. The soft guard tends to absorb bacteria and thus is difficult to clean. In addition, the soft guard blocks plaque into the teeth thereby causing related problems such as gingivitis or peridontal disease. In addition, it stains quickly and needs to be replaced often.

The hard guard and the soft guard are typically formed by two different processes. The first step in producing the hard guard is to create a model of the patient's teeth. This is accomplished by taking an alginate impression of the patient's upper and lower sets of teeth. This is a well known procedure in the art and need not be elaborated upon. The next step is to pour stone into the alginate impressions. The stone can be plaster, Coecal or any other material typically used in the dental industry. The stone is left to set and then a model of the patient's teeth is formed. The upper and lower models are then mounted or articulated using an articulator. The articulation process places the upper and lower models in the proper alignment to incorporate such characteristics as overbites, underbites and crossbites. Proper articulation is important because the night guard and the lower set of teeth must sit together properly when the patient closes his mouth. The model of the upper set of teeth is then taken to be waxed. Enough wax is placed on the model so that the correct vertical is achieved. The vertical is the distance the upper and lower sets of teeth should be separated. The upper model with the wax and the lower model are pressed together so that the lower model teeth make indentations in the wax.

The next step is to flask or invest the model of the upper set of teeth. A flask is a device well known in the art. A flask normally consists of four pieces: the base in which the model is placed; the knockout plate; the top half of the flask; and the lid. The model is placed in the base of the flask. Stone is then mixed and poured into the flask surrounding the model except for the wax portion which is not covered. Once the stone is set, the cast is lubricated with a lubricant such as Vaseline. The lubricant allows the bottom portion of the flask to be separated from the top portion when the top portion is later filled with stone. At that point the top portion of the flask is put in place and stone is poured over the model and the wax, filling the top half of the flask.

After the stone has set, the entire flask is then placed into a boiler. The boiling step causes the wax to melt away. The flask is opened and the lower half of the flask contains the model and the top half of the flask has a U-shaped imprint of the upper set of teeth. The model is then rinsed with a wax solvent to remove any excess wax not eliminated by the boiling process. Next a liquid separating media, such as modern foil, is placed on the model and the top half of the flask with the U-shaped imprint to prevent the acrylic from sticking to the model, or the top half of the flask, when it is placed on the model. A common acrylic used in dental applications is "Vitacrilic" manufactured by Fricke Dental Manufacturing Company. The acrylic is mixed and then left to set for a few minutes at room temperature until it becomes doughy. Once the acrylic is doughy, it can be manually applied to the model so that it completely covers the teeth of the model. A plastic sheet is placed on top of the acrylic to check if there is any porosity or impurities in the acrylic. The upper flask is joined with the lower flask.

The flask is then put under pressure which can range from about 1500–2500 p.s.i.g. The flask is opened and any excess acrylic is removed. The sheet is removed and then the upper half of the flask is again joined with the lower half and the entire flask assembly is put in a vise to exert a constant pressure. Next, the flask and vise are placed into a curing unit to cure for about nine (9) hours at about 165° F. The flask is then opened with the model and acrylic mold bonded together in the lower half of the flask. In order to remove the acrylic mold, the model must be broken. The acrylic mold is then finished by removing the undercuts and polishing and buffing the entire mold thereby producing the hard guard.

The process to make the soft guard is somewhat different. Only one model is needed, that of the upper set of teeth, because articulation is not possible when making a soft guard. A model is made in exactly the same way as in the hard guard process discussed above. The model is then placed in a vacuum-set machine. A sheet of resin manufactured by Healthco is placed in the top of the vacuum-set machine. When the vacuum-set machine is turned on, the resin is heated so that it melts onto the model. Once the machine has completed its operation, the soft guard is basically formed. All that is thereafter required is a few finishing steps such as removing any excess material and cutting certain areas.

Unlike the hard guard process, the soft guard process does not require that the model be broken to remove the guard. The soft guard can be removed easily and quickly because the material does not enter the inner ambrasia of the model. One of the problems with the process for making soft guards, however, is that bubbles may form in the guard due to the vacuum-setting process. Also the soft guard does not sit as well in the user's mouth as the hard guard because it is not articulated.

Accordingly, it is a primary object of the present invention to provide an improved dental guard that is comfortable to wear and less stressful to the user's teeth than conventional hard and soft guards.

Another object of the present invention is to provide a dental guard that can be easily altered to accommodate variations that may occur in the user's mouth without the necessity of producing an entirely new dental guard.

Further objects and advantages will become apparent from the following description and accompanying drawings.

SUMMARY OF THE INVENTION

The dental guard of the present invention is constructed in a two layer fashion. The interior layer, which refers to the layer that makes contact with the user's teeth, is made of a soft material similar to the soft guards. The exterior layer, referring to the layer that is bonded to the soft layer, is made of a hard material. Most dental guards are worn on the upper set of teeth; however, the present invention is not so limited.

The exterior layer is fabricated in a manner similar to the method of fabricating hard guards. One difference, however, is that the interior surface of the exterior layer, to which the soft material will be bonded, is removed. The impressions made from the inner ambrasia and inner proximate of the model are scraped away except for those made by the cusps. They are left so that their impressions are no more than about two millimeters (2 mm) in diameter. The cusps' impressions provide an anchoring point so that the user's teeth can be firmly held in those impressions when the dental guard is complete.

Next the soft layer is fabricated in a manner similar to the hard layer. The hard layer is placed on the model and flasked so that it will be found on the upper half of the flask. Then the soft material is placed on the model and the flask is reassembled joining the model with the soft layer to the hard layer. The device is then put under pressure and cured.

The advantages of the present invention are numerous. The present invention provides a dental guard that has the durability of a hard guard yet the comfort of a soft guard. In addition, the dental guard can be easily altered to accommodate changes in the user's mouth because of its dual layer construction. By simply removing the soft layer and creating a new soft layer, the user has a dental guard modified to his needs quickly and efficiently.

BRIEF DESCRIPTION OF THE DRAWINGS

Exemplary embodiments of the invention summarized above are shown in the accompanying drawings wherein.

DETAILED DESCRIPTION OF THE PREFERRED EMBODIMENT

The guard according to the present invention is fabricated from the following steps. An alginate impression is taken of the patient's upper and lower sets of teeth and then stone is poured into the alginate impression to form the model. This model is duplicated so that two models are available, the original and the duplicate. The duplicate model is used to make the exterior hard layer. The original model will be used for the interior soft layer since it is the most accurate model and the soft layer needs the greatest degree of accuracy.

Figure 1:
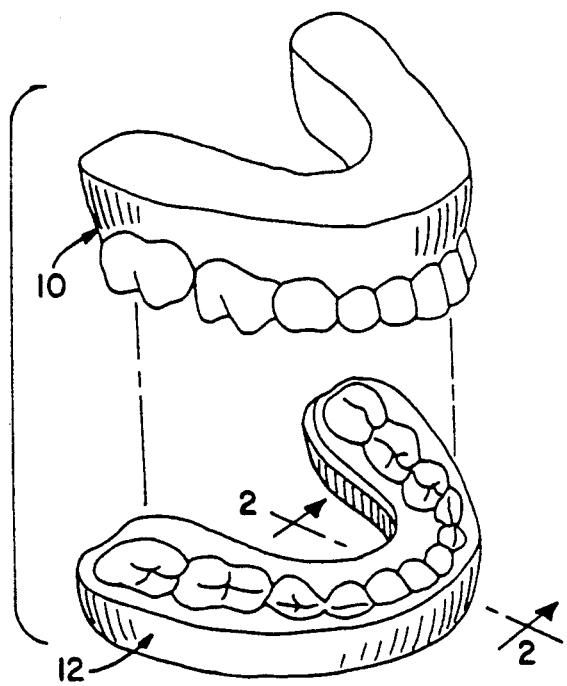
FIG. 1 is a perspective view of a model of a user's upper set of teeth and the unfinished exterior hard layer of the dental guard in accordance with the present invention.
Figure 2:
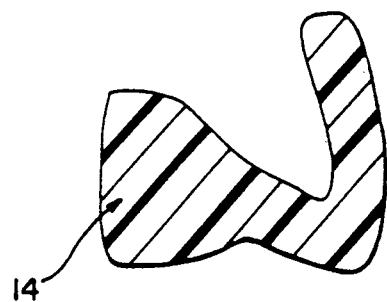
FIG. 2 is a cross-sectional view taken along line 2—2 of the unfinished exterior hard layer of FIG. 1.

Referring now to FIG. 1, there is shown a perspective view of a model 10 of the user's teeth and hard layer 12 of the dental guard. A similar process is used to form hard layer 12 as was described above with respect to a conventional hard guard. Specifically, model 10 of upper and a model of lower (not shown) sets of teeth are articulated. Model 10 of upper set of teeth is waxed to achieve the correct vertical, flasked to create the impression for the hard layer and boiled to remove the wax. Acrylic is then applied to model 10 and the assembly is again flasked resulting in hard layer 12. The hard layer 12 shown in a cross-sectional view in FIG. 2 is illustrative of the conventional hard guards previously described.

Figure 3:
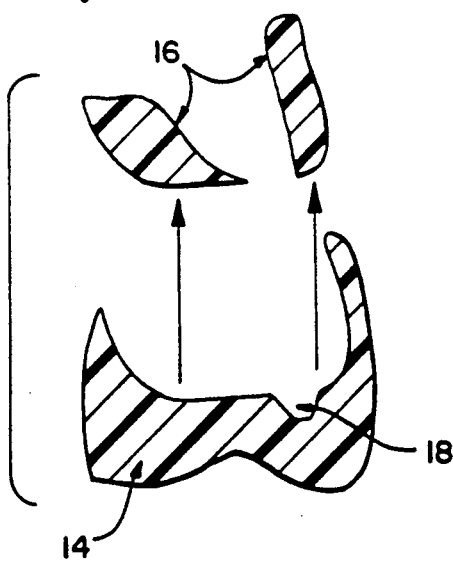
FIG. 3 is a cross-sectional view of the unfinished exterior hard layer with portions of its interior surface removed in accordance with the present invention.

Referring now to FIG. 3, there is shown the removal of interior surface 16 from hard layer 12 (shown in FIG. 1) thereby producing unfinished exterior layer 14. When hard layer 12 of FIG. 1 has been processed so that a hard guard has been formed, approximately eighty to ninety percent (80%-90%) of the interior surface is removed. The facial and lingual impressions are removed by scraping the acrylic with an acrylic burr. Impressions 18 from the cusps are retained to the extent that the diameter of impressions are approximately one to two millimeters (1-2 mm) in diameter.

These impressions 18 are retained because they provide a secure fit when the dental guard is finished. Namely, when the soft layer is bonded to unfinished exterior layer 14, the cusps of the user's teeth will fit snugly in impressions 18. In addition, impressions 18 assure that the vertical will be maintained when the user wears the dental guard.

The original model is now used to create the soft layer. Unfinished exterior layer 14 is placed on the model. Wax is then put around the interface between the exterior layer 14 and the model, sealing any gap therebetween. The process used to make exterior layer 14 initially is substantially duplicated up through the boiling process. Therefore, when the flask is opened, the lower half will contain the model and the upper flask portion will contain unfinished exterior layer 14 in stone. A separating media such as the modern foil referred to previously is placed on both the lower and upper halves of the flask.

The soft material is put on the model and a plastic sheet is placed over it to make sure that there are no bubbles or impurities in the soft material. The soft material used in this preferred embodiment is a soft denture re-base resin sold by General Dental Products, Inc. under the trademark Soft-Pak. The plastic sheet is removed, and the two halves of the flask are brought together. The flask is put under pressure which can range from about 1500 to 2500 p.s.i.g. The flask is again opened so that the model and the soft layer are on one half of the flask and unfinished exterior layer 14 is in the other half of the flask. A monomer or bonding material is placed on the interior surface of exterior layer 14, then the two halves of the flask are again joined. The monomer bonds exterior layer 14 with soft layer 20. The assembly is then placed in a vise and cured for about nine (9) hours at about 165° F. Once guard 22 is cured and removed from the flask, the thickness of exterior layer 14 can be reduced. Guard 22 is finished by polishing and buffing.

Figure 4:
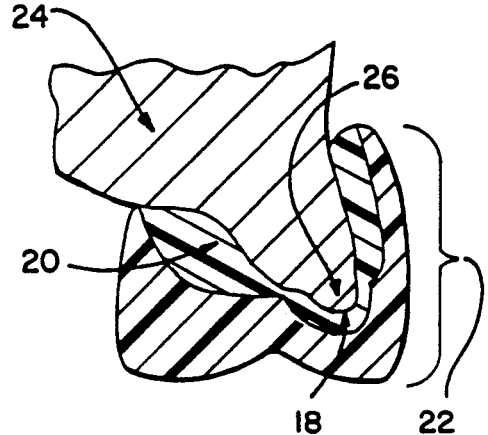
FIG. 4 is a cross-sectional veiw of the finished dental guard worn by the user in accordance with the present invention.

FIG. 4 is a cross-sectional view of the finished dental guard worn by a user. User's tooth 24 only makes contact with soft layer 20. This provides a soft cushion for the teeth and thus makes the guard more comfortable and less stressful to the user. Cusp 26 of the tooth fits snugly in impression 18, thus providing a secure fitting dental guard 22.

Although reference has been made to wearing the dental guard during sleep, the invention is not limited to such a use. The dental guard may be worn by persons during the day for various reasons. In addition, the invention is not limited to a dental guard worn over a user's upper set of teeth. A guard can be made to fit the lower set of teeth, although it is not commonly used in the profession.

What has been described is the best mode of carrying out the invention, though other ways also exist. One other way is to make the hard layer as described and place it on the first model. As before, wax is put around the interface between the hard layer and the model, thereby sealing the gap therebetween. The difference, however, is to extend the wax past the rearmost molar on each side of the mouth to form a tubelike structure behind these molars. The soft material may then be injected through the wax holes into the gap between the model and the hard layer. This process may not be as desirable in some applications because the soft material is thick and tends not to spread well or evenly and may altogether miss some areas.

Another method of carrying out the invention is to use the vacuum-set machine as described above. A sheet of the soft material would be inserted into the vacuum-set machine and melted onto the model. Next a sheet of the hard material would be melted on top of the soft material. This method may result in a vertical of about five millimeters (5 mm) which cannot readily be adjusted, and therefore this method may not be as desirable as the method described above. Further, in this latter method, the guard cannot be articulated.

While this invention has been shown and described in connection with a particular preferred embodiment, it is apparent that certain changes and modifications, in addition to those mentioned above, may be made by those who are skilled in the art without departing from the basic features of the present invention. Accordingly, all such changes and modifications are intended to be covered by the appended claims.

What is claimed is:

1. A dental guard used to protect the teeth of a user comprising:

a hard layer created from an impression of both sets a user's set of teeth, said hard layer comprising an interior surface, said interior surface having a shape conjugate to a first set of the user's teeth wherein said interior surface has been altered to remove facial and lingual impressions created by the first set of teeth and an exterior surface contacting the user's opposite set of teeth when said guard is in use, said exterior surface having indentations from the second set of the user's teeth; and a soft layer bonded to said interior surface of said hard layer, said soft layer having an exterior surface, said exterior surface having a shape conjugate to said interior surface of said hard layer.

2. A dental guard according to claim 1 wherein the sole remaining impressions on said interior surface of said hard layer are from the user's cusps of the first set of teeth.

3. A dental guard according to claim 2 wherein said impressions are of a size no more than two (2 mm) millimeters in diameter in any direction.

4. A dental guard according to claim 1 wherein said first set of teeth is a user's upper set of teeth.

5. A method for making a dental guard comprising the following steps:

forming a hard guard, said hard guard having an interior and an exterior surface;

placing said hard guard on a model of a user's first set of teeth;

sealing any gap between said model and said hard guard;

flasking said model and said hard guard so that said lower half of said flask will contain said model and said upper half of said flask will contain said hard guard when said flasking is completed;

applying a soft layer material to said model;

assembling said flask so that said soft layer material comes in contact with said hard guard;

exerting pressure on said flask causing said soft layer to take the shape of said interior surface of said hard guard;

curing said flask containing said hard guard and said soft layer and;

bonding said soft layer to said hard guard.

6. A method according to claim 5 wherein said first set of teeth is a user's upper set of teeth.

7. A method according to claim 5 wherein the facial and lingual impressions are removed from the interior surface of said hard guard before it is placed on said model.

8. A method according to claim 7 wherein impressions left from cusps of model's teeth are preserved in said hard guard.

9. A method according to claim 8 wherein said impressions from said cusps are no more than about two millimeters (2 mm) in diameter.

10. A method for making a dental guard comprising the following steps:

forming a hard guard;

placing said hard guard on a model of a user's first set of teeth; sealing any gap between said model and said hard guard with wax;

forming two tube-like structures with said wax behind a rear-most molar on each side of said model;

injecting a soft material through said tube-like structures so that said soft material will spread between said model and said hard guard, bonding to said hard guard; and removing said bonded hard and soft material.

11. A dental guard used to protect a first set of teeth having a first profile comprising:
- a hard layer comprising an interior surface and an exterior surface;
- said interior surface of said hard layer comprising impressions having a shape conjugate to said first profile;
- a soft layer having an inner surface and an outer surface,
- said inner surface is in contact with said interior surface and comprises impressions having a shape similar to the first profile,
- said outer surface comprises impressions having a shape conjugate to said first profile.

12. A dental guard according to claim 11 wherein said exterior surface of said hard layer comprising impressions having a shape conjugate to a second profile of a second set of teeth.

13. A dental guard according to claim 11 wherein said interior surface of the hard layer has been altered to remove facial and lingual impressions created by the first set of teeth.

14. A dental guard according to claim 11 wherein said interior surface impressions have the shape of the front face of the first set of teeth.

15. A dental guard according to claim 11 wherein said hard layer has a biting surface which has the shape of an impression of a second set of teeth.

* * * * *